(12) United States Patent  
Josse et al.

(10) Patent No.: US 9,244,051 B2
(45) Date of Patent: Jan. 26, 2016

(54) DETECTION OF HYDROCARBONS IN AQUEOUS ENVIRONMENTS

(71) Applicants: Fabien J. Josse, Brookfield, WI (US); Florian Bender, Milwaukee, WI (US); Antonio J. Ricco, Los Gatos, CA (US); Rachel Mohler, Emeryville, CA (US); Urmas Kelmser, San Ramon, CA (US); Karen Synowiec, Martinez, CA (US); Robert Michael Lorenz, Walnut Creek, CA (US)

(72) Inventors: Fabien J. Josse, Brookfield, WI (US); Florian Bender, Milwaukee, WI (US); Antonio J. Ricco, Los Gatos, CA (US); Rachel Mohler, Emeryville, CA (US); Urmas Kelmser, San Ramon, CA (US); Karen Synowiec, Martinez, CA (US); Robert Michael Lorenz, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 40 days.

(21) Appl. No.: 13/934,347

(22) Filed: Jul. 3, 2013

(65) Prior Publication Data

US 2014/0011285 A1 Jan. 9, 2014

Related U.S. Application Data

(60) Provisional application No. 61/667,763, filed on Jul. 3, 2012.

(51) Int. Cl.
*G01N 33/18* (2006.01)
*G01N 29/02* (2006.01)
*G01N 1/40* (2006.01)

(52) U.S. Cl.
CPC ............ *G01N 33/1826* (2013.01); *G01N 1/405* (2013.01); *G01N 29/022* (2013.01);
(Continued)

(58) Field of Classification Search
CPC ....... G01N 29/02; G01N 29/022; G01N 1/40; G01N 1/405; G01N 33/18; G01N 33/1833; G01N 33/1826; G01N 2291/0255; G01N 2291/0256; G01N 2291/02809; G01N 2291/0422; G01N 2291/0423; G01N 2291/106; Y10T 436/21; Y10T 436/212; Y10T 436/214; Y10T 436/216; Y10T 436/255; Y10T 436/2575

USPC ............... 436/25, 28, 60, 139–142, 147, 157, 436/174, 177, 178, 180; 422/68.1, 69, 422/82.12, 527; 210/679
See application file for complete search history.

(56) References Cited

U.S. PATENT DOCUMENTS 5,469,369 A * 11/1995 Rose-Pehrsson et al. ...... 702/27
6,902,701 B1 * 6/2005 Hughes et al. .................. 422/83
(Continued)

FOREIGN PATENT DOCUMENTS

WO 99/66304 12/1999

OTHER PUBLICATIONS

Ho et al. Sensors, vol. 3, pp. 236-247, 2003.*
(Continued)

*Primary Examiner* — Maureen Wallenhorst
(74) *Attorney, Agent, or Firm* — Frank C. Turner; Melissa Patangia; Carlos L. Hanze (57) ABSTRACT

A process for a pre-concentration unit including: a sorbent material coated passage-way having an entrance for receiving a hydrocarbon-containing groundwater sample and for pre-concentrating the hydrocarbons in a hydrocarbon-containing groundwater sample by successive sorption/desorption cycles, and having an exit for discharging the pre-concentrated hydrocarbons; a heating unit for heating the sorbent material coated passage-way; and; an array of shear horizontal-surface acoustic wave sensors with coatings adapted for detecting and quantifying the pre-concentrated hydrocarbons, disposed at the exit of the sorbent material coated passage-way; and a housing for enclosing the pre-concentration unit and the array of shear horizontal-surface acoustic wave sensors, adapted for continuous use at a body of hydrocarbon-containing groundwater, and coupled to mathematical methods for generating concentrations of specific analytes from both transient and steady-state signals.

15 Claims, 6 Drawing Sheets (52) U.S. Cl.
CPC .... *G01N2291/0255* (2013.01); *G01N 2291/0256* (2013.01); *G01N 2291/02809* (2013.01); *G01N 2291/0422* (2013.01); *G01N 2291/0423* (2013.01); *G01N 2291/106* (2013.01); *Y10T 436/21* (2015.01); *Y10T 436/255* (2015.01)

(56) References Cited

U.S. PATENT DOCUMENTS

| | | | |
|---|---|---|---|
| 7,053,522 B1* | 5/2006 | da Cunha | 310/313 A |
| 2005/0065446 A1 | 3/2005 | Talton | |
| 2007/0084347 A1* | 4/2007 | Boyle et al. | 96/101 |
| 2008/0148815 A1 | 6/2008 | Lucas et al. | |
| 2008/0289397 A1 | 11/2008 | Hassan et al. | |
| 2009/0090197 A1* | 4/2009 | Finlay et al. | 73/863.12 |
| 2012/0223226 A1* | 9/2012 | Rafferty et al. | 250/288 |

OTHER PUBLICATIONS

Mensah-Brown et al. IEEE Sensors Journal, vol. 12, No. 5, May 2012, pp. 893-903.*

Notification of Transmittal of the International Search Report and the Written Opinion of the International Searching Authority, or the Declaration; International Application No. PCT/US2013/049185; dated Nov. 4, 2013.

Bender et al., "Influence of Ambient Parameters on the Response of Polymer-Coated SH-Surface Acoustic Wave Sensors to Aromatic Analytes in Liquid-Phase Detection", 2011 Joint Conference of the IEEE IFCS and EFTF Proc., pp. 422-427.

Josse et al., "Guided Shear Horizontal Surface Acoustic Wave Sensors for Chemical and Biochemical Detection in Liquids", Anal. Chem. 73(2001) pp. 5937-5944.

Josse et al., "Guided SH-SAW Sensors for Liquid-Phase Detection", Proc. IEEE Int. Freq. Control Symp. (2001) pp. 454-461.

Bender et al., "Love-Wave Biosensors Using Cross-Linked Polymer Waveguides on $LiTaO_3$ Substrates", Electronics Lett. 36 (2000) pp. 1672-1673.

Deeb et al. MTBE and Other Oxygenates: Environmental Sources, Analysis, Occurrence, and Treatment, Environ. Eng. Sci. 20 (2003) pp. 433-447.

Wang et al., "Forensic Fingerprinting of Biomarkers for Oil Spill Characterization and Source Identification", Environ. Forensics 7 (2006) pp. 105-146.

Duran et al, "Thermal desorption pre-concentrator based system to assess carbon dioxide contamination by benzene", Sens. Actuators B 131(2008) pp. 85-92.

Groves et al., "Surface acoustic wave (SAW) microsensor array for measuring VOCs in drinking water", J. Environ. Monit. 8(2006) pp. 932-941.

Lichtenberg et al., Sample pretreatment on microfabricated devices, Talenta 56(2002) pp. 233-266.

* cited by examiner

DETECTION OF HYDROCARBONS IN AQUEOUS ENVIRONMENTS

PRIORTITY CLAIM AND CROSS-REFERENCE TO RELATED APPLICATION

The present patent application claims priority to U.S. patent application Ser. No. 61/667,763, filed on Jul. 3, 2012, entitled "System for Detection and Monitoring of Hydrocarbons in Aqueous Environments," which is herein incorporated by reference in its entirety.

FIELD OF THE INVENTION

The present invention is directed to a system and process for detection of hydrocarbons in aqueous environments, and more specifically, to pre-concentration and guided shear horizontal-surface acoustic wave sensor-based detection and monitoring of hydrocarbons in aqueous environments.

BACKGROUND OF THE INVENTION

Underground storage tanks ("USTs") for fuel and oil are commonly used, and from time to time may be prone to unintended leakage. Nearly 600,000 federally regulated USTs exist in the United States, and approximately 6,000 leaks are recorded annually as reported by the U.S. Environmental Protection Agency. As such, it is desirable to detect and monitor groundwater in situ in the vicinity of USTs.

Detection of organic compounds can be performed using various sensor technologies, including acoustic-wave, optical and resistive technologies. However, when used without pre-concentration, real-time sensor technologies can detect only some relevant analytes at the required concentration levels, but others are hard to detect, such as benzene which may require detection at levels in the order of 5 ppb (5 $\mu$g/L). While sample pre-concentration in the gas phase is a well known, a need remains for pre-concentration of volatile organic compounds in the aqueous phase.

Sensors are known for determining benzene concentrations at low levels is the gas phase, but not in water. The use of traditional analysis methods requires technicians to visit the field, preserve the samples and then ship samples to a lab. Typically, results for these traditional analyses are not reported for two or more weeks. An improved method of monitoring dissolved hydrocarbons in groundwater is desired.

SUMMARY OF THE INVENTION

The present integrated system and process is directed to a pre-concentrator and guided shear horizontal-surface acoustic wave ("SH-SAW") device for sensor-based detection and monitoring of hydrocarbons in aqueous environments. This new on-site detection and monitoring system seeks to generate results for analytes of interest.

In one embodiment, the invention is a device including a pre-concentration unit comprising: a passage-way containing a sorbent material with an entrance for receiving a hydrocarbon-containing groundwater sample and for pre-concentrating the hydrocarbons in a hydrocarbon-containing groundwater sample by single or successive iterative sorption/desorption cycles, and having an exit for discharging the pre-concentrated hydrocarbons; a heating unit for heating the passage-way containing a sorbent material; and an array of shear horizontal-surface acoustic wave sensors with coatings adapted for detecting and quantifying the pre-concentrated hydrocarbons, disposed at the exit of the sorbent material coated passage-way; and a housing for enclosing the pre-concentration unit and the array of shear horizontal-surface acoustic wave sensors, adapted for continuous use in a body of hydrocarbon-containing groundwater.

This invention will include the use of mathematical methods to predict the steady-state response from the transient signals well before equilibrium as well as deconvolve the signal to generate concentration values for the analytes of interest.

In another embodiment, the invention is a method of on-site detection of hydrocarbons in groundwater using the device of the invention.

BRIEF DESCRIPTION OF THE DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings.

DETAILED DESCRIPTION OF THE INVENTION

The following detailed description refers to the accompanying drawings. Wherever possible, the same reference numbers are used in the drawings and the description to refer to the same or similar parts. Also, similarly-named elements may perform similar functions and may be similarly designed, unless specified otherwise. Numerous details are set forth to provide an understanding of the described embodiments. The embodiments may be practiced without these details. In other instances, well-known methods, procedures, and components have not been described in detail to avoid obscuring the described embodiments. While several exemplary embodiments and features are described here, modifications, adaptations, and other implementations may be possible, without departing from the spirit and scope of the invention. Accordingly, unless stated otherwise, the descriptions relate to one or more embodiments and should not be construed to limit the invention as a whole. Instead, the proper scope of the invention is defined by the appended claims.

The present invention relates to a system and method for detecting and monitoring comprised of a pre-concentration unit and acoustic-wave devices based detection for volatile organic compounds directly in the aqueous phase. The invention is intended to be suitable for implementation in existing groundwater monitoring wells as they exist at numerous locations, such as UST sites, refineries and terminals.

In one embodiment, the invention includes a pre-concentration unit having a substrate and sorbent material which sorbs organic compounds from a water sample, which will then be released when heated to a specific temperature. Since aqueous phases do not permit excessive heating, the pre-concentration unit in one embodiment is a multi-step system. The pre-concentrated sample is then detected in an array of SH-SAW sensors with various coatings. By evaluating both steady-state signal shift and time dependence of response (known as the transient response), one or several organic compounds present in the sample can be detected and quantified.

Figure 1:
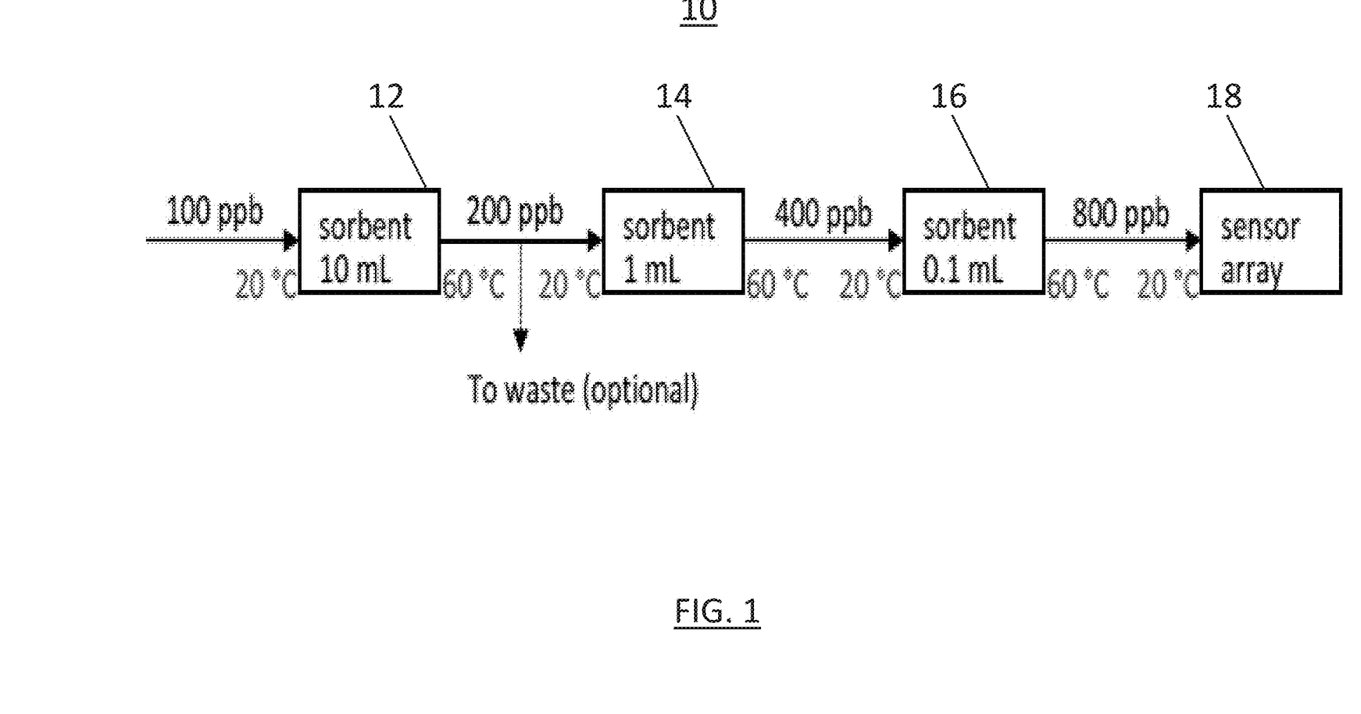
FIG. 1 is a flow diagram of a process for detecting hydrocarbons in aqueous environments in accordance with an embodiment of the present invention.

The invention includes a pre-concentration unit (which can be a multi-step system) and an array of acoustic-wave based sensors for selective detection and quantification of volatile organic compounds in-situ in the aqueous phase. A non-limiting example of the multi-step system is shown in FIG. 1. FIG. 1 shows a hypothetical example of how an aqueous sample is successively exposed to sorbent materials and heated to perform the pre-concentration.

Figure 2:
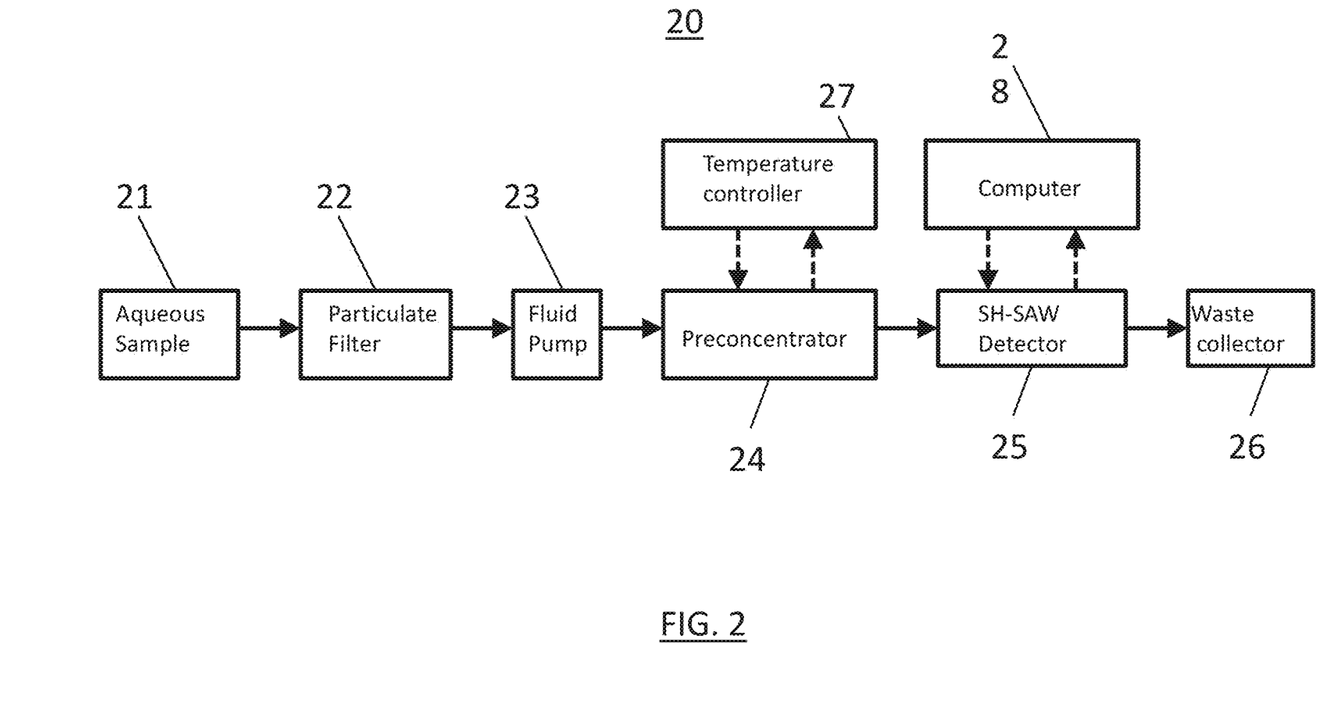
FIG. 2 is a block diagram of a system for detecting hydrocarbons in aqueous environments in accordance with an embodiment of the present invention.

FIG. 2 is a block diagram of a system 20 for in situ detection in groundwater in accordance with an embodiment of the present invention. The solid black arrows show the flow of liquid containing the hydrocarbons to be anaylzed, and the dashed black arrows show the direction of information and control. In accordance with the system shown in FIG. 2, an aqueous sample 21 is optionally diverted through a particulate filter 22 to remove undesired particulates from the aqueous sample to be analyzed. The sample is then pumped via fluid pump 23 to a pre-concentrator unit 24 that performs a successive or "iterative" pre-concentration process as described with reference to FIG. 1. In the pre-concentration unit 24, the aqueous sample (filtered or unfiltered) is collected, gathered or otherwise contained within or in communication with a first sample collector at ambient temperature. The sample collector 24 is preferably constructed of a first sorbent material, and is optionally coupled to a particulate filter (not shown) for removing undesired particulates from the aqueous sample.

After a suitable collection time, which duration may depend on the compound to be analyzed, a heater will heat the sample to promote the release of sorbed analytes from sample collector 24. If a still higher concentration ratio is desired, such pre-concentrated sample is then pumped to a second sorbent phase where the pre-concentration process is repeated, etc. The indicated concentrations (in ppb=μg/L) in FIG. 1 schematically show how the concentration of an analyte in the sample might increase with each pre-concentration step (exact concentration values are arbitrary, as are the temperatures and volumes of the various sorbent phases shown). Alternatively, a higher concentration ratio can be achieved in a more continuous form, where a heated zone is passing through a pre-concentration unit with the same velocity as a simultaneously pumped sample; the concentration of volatile hydrocarbons in the sample will then continuously increase as the latter is proceeding through the pre-concentration unit (not shown). At the end of the multi-step system, the pre-concentrated sample will be detected in a sensor array which, e.g., might consist of multiple SH-SAW (shear-horizontal surface acoustic wave) sensors with different coatings, which will sorb the relevant analytes from the sample and induce a response signal in the sensors.

In accordance with one non-limiting embodiment of the present invention, the pre-concentration unit (or pre-concentrator) includes a flow path through a selected sorbent material that exposes organic analyte in aqueous solution to a selective coating, favors sorption of the analyte, which is subsequently desorbed via thermal release (heating). General design parameters for the pre-concentration unit include: (1) the capacity of pre-concentration (e.g., chemistry of selective coating, thickness of coating, coating on a substrate filler, such as beads, and flow path length, total amount of coating material); and (2) the efficiency of heat transfer for release (e.g., material the device is made of, thickness of the material, exposure to heat; such as areas that heat is applied and cross sectional area of flow path, and flow rate).

The coating is a chemical species that must be effective in both the sorption and (thermally induced) desorption of the analyte of interest in comparison to other analytes in the aqueous phase. The amount or mass of coating material relates to the size of the concentrated fluid volume released; more coated material will result in a larger sample volume for the detector to measure. In order to optimize sorption and desorption, a thinner film (a few microns or less) is favorable, with larger surface area, hence coating on a support substrate (polymer or glass beads, or glass fibers are examples).

The thermal release of sorbed analyte can be achieved by applying resistive heating. Metal wires or patterned metal films can be used to generate heat. Heating wire is more convenient to use with a cylindrical configuration (see for example FIG. 3) because it can be more easily wrapped around the exterior of tubing, than a flat heater pad. Planar configurations (see for example FIG. 4) can take advantage of flat pre-manufactured heating pads. The option also exists to integrate heating elements into a planar device if fabrication techniques for miniaturization are used, such as depositing thin metal films by evaporation. With heating elements integrated into the device, very precise heating is possible, to minimize power consumption and maximize efficiency. One additional consideration is that the heating needs to warm the aqueous phase without boiling or causing as gas phase to develop, therefore temperature sensors and a heating controller are needed.

Figure 3:
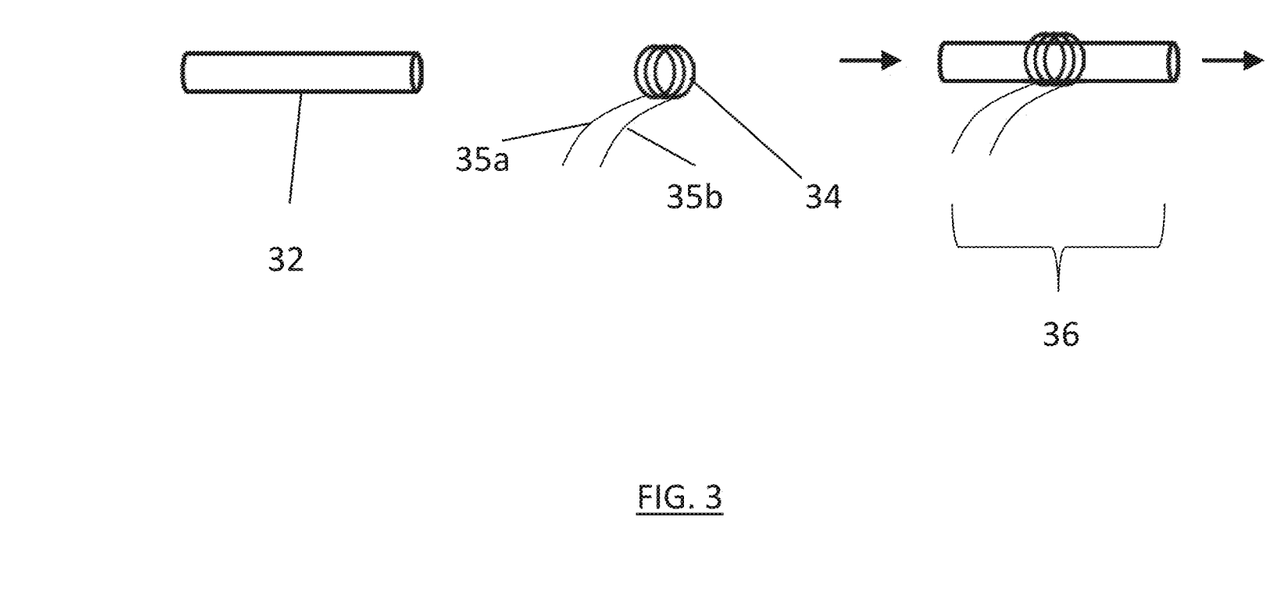
FIG. 3 is an illustration of an assembled cylindrical pre-concentration unit in accordance with an embodiment of the present invention.
Figure 4:
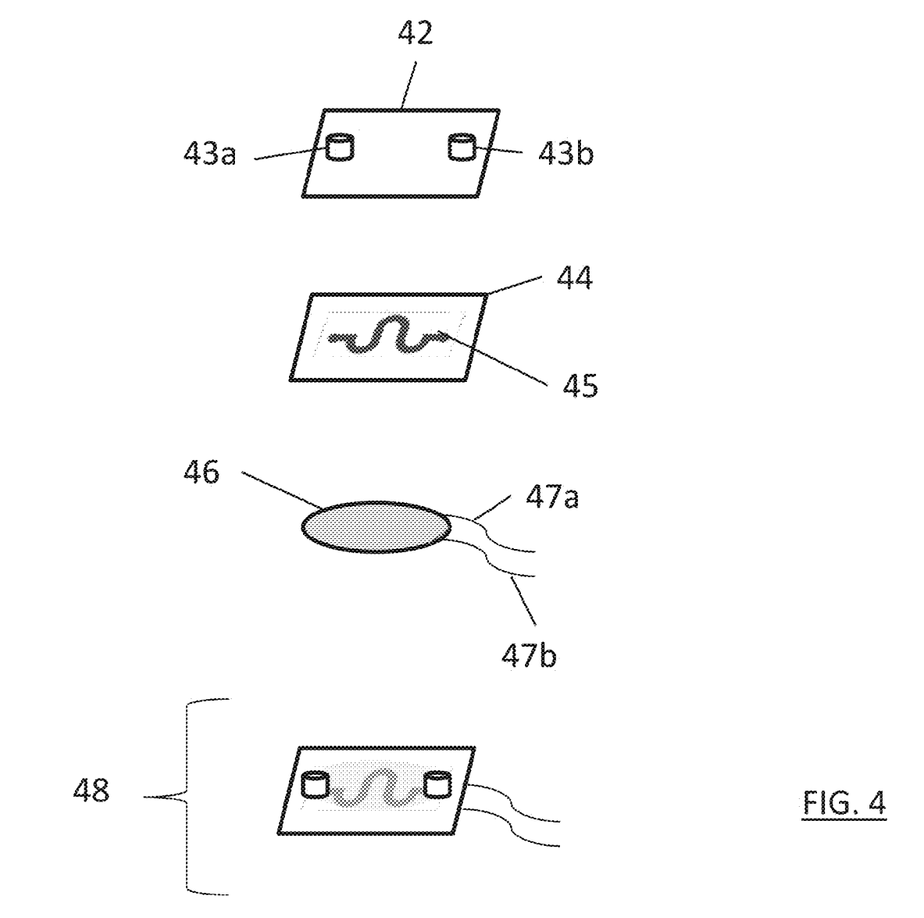
FIG. 4 is an illustration of an assembled planar pre-concentration unit in accordance with an embodiment of the present invention.

Referring now to FIGS. 3 and 4, the pre-concentration units may be cylindrical or planar. A cylindrical design is typically more convenient to assemble due to readily available connections and tubing; planar designs, however, have the potential for more dense fluidic channels and more efficient heating, which may result in more efficient pre-concentration FIG. 3 shows a finally-assembled cylindrical pre-concentration unit 36 in accordance with an embodiment of the present invention. Solid black arrows show the flow of the liquid. The pre-concentration unit 36 includes a passageway (or conduit) 32 and a heater element 34. The heater element 34 can be in the form of a coil that is in communication with the conduit 32 so as to enable heat transfer and cause heating of the conduit 32 and thus heating of the aqueous sample passing therethrough. The coil can be heated, for example, via an electrical source coupled to leads 35a and 35b.

Cylindrical flow paths can be constructed using commonplace tubing materials, such as metal tubing (copper or stainless steel), polymer plastic (PTFE, PET, PEEK . . . etc.), or glass. Because of the inherent symmetry of such materials, the radius is constant and a circular cross section exists. When using machining or semiconductor fabrication techniques to form the flow path, the shape will be rectangular or trapezoidal. Depending on the aspect ratio (defined as the ratio of height to width) of the cross sectional area, both shallow and wide (low aspect ratio) or tall and narrow (high aspect ratio) flow paths may be formed. While physical flow properties are similar in non-cylindrical versus cylindrical flow paths, some differences exist, and may need to be considered when understanding device performance.

FIG. 4 shows as finally-assembled planar pre-concentration unit 48 in accordance with an embodiment of the present invention. The planar pre-concentration unit 48 includes a top plate 42 with fluid/tubing connectors 43a and 43b, a bottom plate 44 with fluid flow path (including coating) 45, and a heater pad 46 for bottom plate 44. Connections 43a and 43b can be machined from metal, or made of plastic materials and attached to the top plate 42 with an epoxy. Leads 47a and 47b are provided for coupling the heater pad 46 to an electrical source. Components 42-48 can be "sandwich" stacked and held together with bolts, epoxy or other means (not shown) to form the finally-assembled planar pre-concentration unit 48.

Optionally, a chemically inert O-ring, flat gasket or other sealing component can be arranged between the top plate 42 and bottom plate 44 to prevent leakage of fluid from the flow path 45.

Planar configurations are advantageous for miniaturization: commercial fabrication techniques used to manufacture small features are designed for planar formats. Heating is easier to achieve as well, due to the large flat surface area, and thin material thickness (favoring rapid heating), with the heating element only needing attachment in two dimensions (cylindrical needs three, for the curved surface) which makes the device more durable than cylindrical tubing. Planar configuration is also amenable to stacking, if more than one concentration stage is desired.

Figure 5:
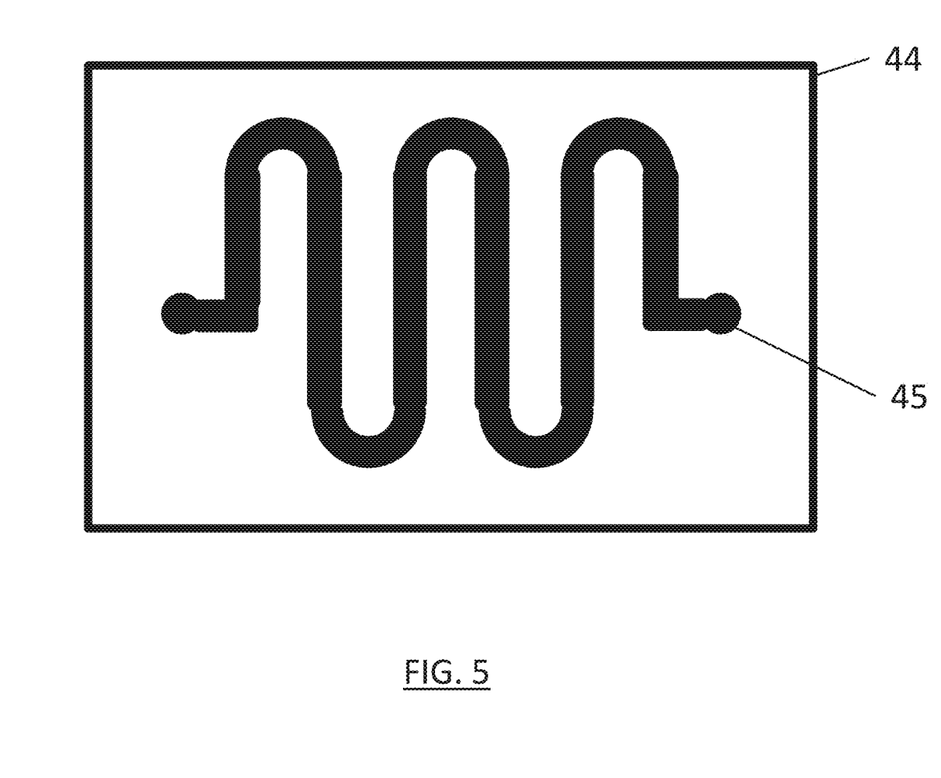
FIG. 5 is an illustration of an exemplary serpentine flow path for a planar pre-concentration unit in accordance with an embodiment of the present invention.
Figure 6:
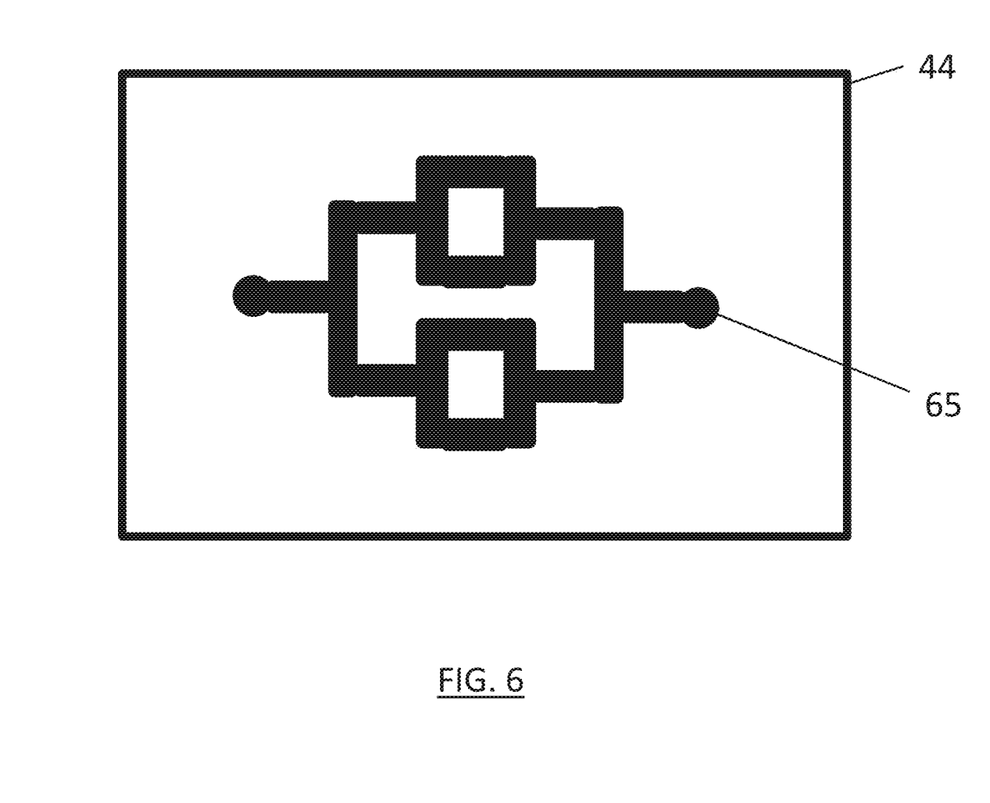
FIG. 6 is an illustration of an exemplary bifurcated flow path for a planar pre-concentration unit in accordance with an embodiment of the present invention.

FIG. 5 shows an exemplary, non-limiting flow path 45 for a planar pre-concentrator unit. As shown in FIG. 5, a serpentine channel of bifurcated grooves can be used as a configuration for the flow path. Alternatively, a bifurcated design as shown in FIG. 6 may be advantageous and less prone to the effects of clogging. With a bifurcated design 65, the entrance channel is split into two channels, those two split into two, etc., then reversed (two combines to one) to result in one channel leaving the device. The bifurcated design 65 is less sensitive to clogging: if a clog occurs in the split channels, flow continues in the other parallel channels. It is also less demanding on pumps and easier to machine. The bifurcated design, however, does not have the ability to create as dense features as the serpentine design. Feature density is a consideration, where increasing feature density results in an increase in concentrated sample volume.

In accordance with another embodiment, the top and bottom plates of a planar device can be fabricated from brass, aluminum, stainless steel and other metals that are favorable for efficient conduction of heat. However, challenges arise when attempting to use conventional machining methods for small flow path dimensions (<800 microns). For miniaturization on the scale of tens to hundreds of microns, semiconductor fabrication methods are available, and common substrates are silicon and glass. Semiconductor methods also provide the option for integrating heating systems or selective coatings. Polymer materials are possible but less desirable due to poor thermal conduction and some machining limitations.

The heating device used with the planar pre-concentration device is a metal film heater: this was chosen because of the efficiency of design (it can apply heating to a large area without adding bulk to the device). The heat element is applied to the thinner of the metal plates (the plate with the fluid channels because the thin metal walls will transfer the heat more efficiently (due to reduced thermal mass) to the aqueous phase to desorb the concentrated analyte. The thin heater is also beneficial in that it can quickly reach temperature (on the order of seconds) and consequently heat the liquid phase (on the order of a minute).

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as that term is interpreted as a transitional word in a claim.

What is claimed is:

1. A system for in situ monitoring of groundwater, comprising:
   a. a pre-concentration unit comprising:
      a sorbent material coated passage-way having an entrance configured for receiving a sample of groundwater containing a hydrocarbon and for pre-concentrating the hydrocarbon contained in the sample by successive sorption/desorption cycles, and having an exit configured for discharging a pre-concentrated hydrocarbon-containing aqueous sample; and
      a heating unit for heating the sorbent material coated passage-way;
   b. an array of shear horizontal-surface acoustic wave sensors with coatings configured for detecting the pre-concentrated hydrocarbon-containing aqueous sample, disposed at the exit of the sorbent material coated passage-way of the pre-concentration unit; and
   c. a housing enclosing the pre-concentration unit and the array of shear horizontal-surface acoustic wave sensors.

2. The system according to claim 1, wherein the housing is configured for continuous use in at a body of hydrocarbon-containing groundwater.

3. The system according to claim 1, wherein output of the system indicates the species and concentrations of one or more hydrocarbons in the groundwater sample.

4. The system according to claim 1, further comprising a computer processor in communication with the acoustic wave sensors, the processor configured to receive signals for the acoustic wave sensors and to execute a computer executable code responsive to the signals, the computer executable code comprising code for calculating an equilibrium concentration corresponding to a specific analyte.

5. The system according to claim 1, further comprising a controller in communication with the heating unit for controlling the heating of the sorbent material coated passage-way.

6. The system according to claim 1, wherein the pre-concentration unit is a cylindrical pre-concentration unit.

7. The system according to claim 1, wherein the pre-concentration unit is a planar pre-concentration unit.

8. The system according to claim 7, wherein the planar pre-concentration unit comprises a serpentine passage-way.

9. The system according to claim 7, wherein the planar pre-concentration unit comprises a bifurcated passage-way.

10. The system of claim 1, wherein the sorbent material coated passage-way comprises a continuous coating of the sorbent material from the entrance to the exit.

11. The system of claim 1, wherein the pre-concentration unit comprises a second sorbent material coated passage-way having an entrance for receiving the pre-concentrated hydrocarbon-containing aqueous sample and for further pre-concentrating the hydrocarbon contained in the sample by successive sorption/desorption cycles; and a second heating unit for heating the second sorbent material coated passage-way.

12. A method for in situ monitoring of groundwater, comprising passing groundwater containing a hydrocarbon to a device comprising a pre-concentration unit comprising a sorbent material coated passage-way and a heating unit for heating the sorbent material coated passage-way, pre-concentrating the hydrocarbon in the groundwater by successive sorption/desorption cycles in the sorbent material coated passage-way, discharging a pre-concentrated hydrocarbon-containing aqueous sample from the pre-concentration unit by heating the sorbent material coated passage-way; and detecting the pre-concentrated hydrocarbon-containing aqueous sample in an array of shear horizontal-surface acoustic wave sensors with coatings for detecting the aqueous pre-concentrated hydrocarbon sample wherein an output of the device indicates the species of hydrocarbons in the hydrocarbon-containing groundwater.

13. The method of claim 12, wherein the heating of the sorbent material coated passage-way warms the hydrocarbon-containing groundwater in the passageway without boiling or causing a gas phase to develop.

14. The method of claim 13, wherein the successive sorption/desorption cycles comprise exposing the hydrocarbon-containing groundwater to the sorbent material coated passage-way and in multi-steps heating successive zones of the coated passage-way to promote the release of sorbed analytes.

15. The method of claim 13, wherein the successive sorption/desorption cycles comprise exposing the hydrocarbon-containing groundwater to the sorbent material coated passage-way and passing a heated zone through the pre-concentration unit with the same velocity as the hydrocarbon-containing groundwater to promote the release of sorbed analytes.

* * * * *